(12) United States Patent
Puno et al.

(10) Patent No.: US 7,875,080 B2
(45) Date of Patent: Jan. 25, 2011

(54) INTERVERTEBRAL SPACER

(75) Inventors: Rolando Puno, Prospect, KY (US);
Michael O'Brien, Pinecrest, FL (US);
William J. Albans, Cordova, TN (US);
Scott Gareiss, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1311 days.

(21) Appl. No.: 10/985,237

(22) Filed: Nov. 10, 2004

(65) Prior Publication Data

US 2006/0100705 A1    May 11, 2006

(51) Int. Cl.
*A61F 2/44* (2006.01)
(52) U.S. Cl. .................................. 623/17.16
(58) Field of Classification Search .... 623/17.11–17.16
See application file for complete search history.

(56) References Cited

U.S. PATENT DOCUMENTS

| | | | |
|---|---|---|---|
| 4,834,757 A | 5/1989 | Brantigan | |
| 5,397,364 A | 3/1995 | Kozak et al. | |
| 5,609,635 A | 3/1997 | Michelson | |
| 5,609,637 A | 3/1997 | Biedermann et al. | |
| 5,702,450 A | 12/1997 | Bisserie | |
| 5,865,845 A | 2/1999 | Thalgott | |
| 5,888,222 A | 3/1999 | Coates et al. | |
| 5,989,289 A | 11/1999 | Coates et al. | |
| 6,143,033 A | 11/2000 | Paul et al. | |
| 6,245,108 B1 | 6/2001 | Biscup | |
| 6,425,140 B1 | 7/2002 | Vitches | |
| 6,425,920 B1 | 7/2002 | Hamada | |
| 6,432,106 B1 | 8/2002 | Fraser | |
| 6,458,159 B1 | 10/2002 | Thalgott | |
| 6,468,311 B2 | 10/2002 | Boyd et al. | |
| 6,482,233 B1 | 11/2002 | Aebi et al. | |
| 6,511,509 B1 | 1/2003 | Ford et al. | |
| D472,971 S | 4/2003 | Anderson | |
| D473,944 S | 4/2003 | Anderson | |
| 6,554,863 B2 | 4/2003 | Paul et al. | |
| 6,558,424 B2 | 5/2003 | Thalgott | |
| 6,610,093 B1 | 8/2003 | Pisharodi | |
| 6,635,086 B2 | 10/2003 | Lin | |
| 6,660,038 B2 | 12/2003 | Boyer, II et al. | |
| 6,716,245 B2 | 4/2004 | Pasquet et al. | |
| 6,719,794 B2 | 4/2004 | Gerber et al. | |
| 7,137,997 B2* | 11/2006 | Paul ........................ | 623/17.11 |
| 2001/0047208 A1 | 11/2001 | Michelson | |
| 2002/0029084 A1 | 3/2002 | Paul et al. | |
| 2002/0087212 A1 | 7/2002 | James et al. | |
| 2002/0193880 A1 | 12/2002 | Fraser | |
| 2003/0023312 A1 | 1/2003 | Thalgott | |

(Continued)

FOREIGN PATENT DOCUMENTS

DE    29611595 U1    9/1996

(Continued)

*Primary Examiner*—Anu Ramana

(57) ABSTRACT

An interbody spacer for insertion between vertebral members. The spacer includes a body having posterior and anterior sides, and inferior and superior faces. The spacer further includes a plurality of teeth to maintain the position of the spacer between the vertebral members. The teeth are aligned in a pattern and have a shape to allow insertion into the space between the vertebral members, and prevent or limit movement once the spacer is positioned in the space.

27 Claims, 11 Drawing Sheets

U.S. PATENT DOCUMENTS

| | | |
|---|---|---|
| 2003/0028249 A1 | 2/2003 | Baccelli et al. |
| 2003/0040709 A1 | 2/2003 | Mason |
| 2003/0040799 A1 | 2/2003 | Boyd et al. |
| 2003/0125739 A1 | 7/2003 | Bagga et al. |
| 2003/0130737 A1 | 7/2003 | McGahan et al. |
| 2003/0139813 A1 | 7/2003 | Messerli et al. |
| 2004/0002761 A1 | 1/2004 | Rogers et al. |
| 2004/0039448 A1 | 2/2004 | Pisharodi |
| 2004/0073310 A1 | 4/2004 | Moumene et al. |
| 2004/0122518 A1 | 6/2004 | Rhoda |

FOREIGN PATENT DOCUMENTS

| | | |
|---|---|---|
| EP | 0 042 271 | 12/1981 |
| EP | 0860152 A2 | 8/1998 |
| EP | 0860152 A3 | 9/1998 |
| EP | 1 138 285 | 10/2001 |
| WO | WO 01/03615 | 1/2001 |
| WO | WO 01/91686 | 12/2001 |
| WO | WO 02/080819 | 10/2002 |
| WO | WO 03/053290 | 7/2003 |

\* cited by examiner

# INTERVERTEBRAL SPACER

BACKGROUND

A large majority of the population will experience back pain at some point in their lives that results from a spinal condition. The pain may range from general discomfort to disabling pain that immobilizes the individual. The back pain may result from a trauma to the spine, be caused by the natural aging process, or may be the result of a degenerative disease or condition.

Procedures to remedy these problems may require correcting the spacing between vertebral members by inserting a spacer. The spacer is carefully positioned within the disc space and aligned relative to the vertebral members. The spacer is sized to position the vertebral members in a manner to alleviate the back pain.

The spacers often include teeth that extend outward from the body of the spacer to maintain the position of the spacer relative to the vertebral members. Various styles and shapes of teeth have been used previously to prevent movement after insertion into the disc space. Further, the teeth may be located along a single face of the spacer, multiple faces, or along limited areas along one or more faces.

The spacer and teeth should also be designed to facilitate insertion into the disc space. Teeth designs that limit or prevent movement of the spacer relative to the vertebral members may not be practical as they make the spacer too difficult to insert into the disc space.

SUMMARY

One embodiment of the present invention is directed to an interbody spacer for positioning between vertebral members. The spacer may include a body having anterior and posterior walls, and opposing first and second faces. The spacer may further include a plurality of teeth oriented to allow for inserting the spacer into the space between the vertebral members, and prevent or limit movement once the spacer is positioned.

The teeth may be located on one or both of the first and second faces. The teeth may be positioned within a limited section or sections, or across the entirety of the faces.

DETAILED DESCRIPTION

Figure 1:
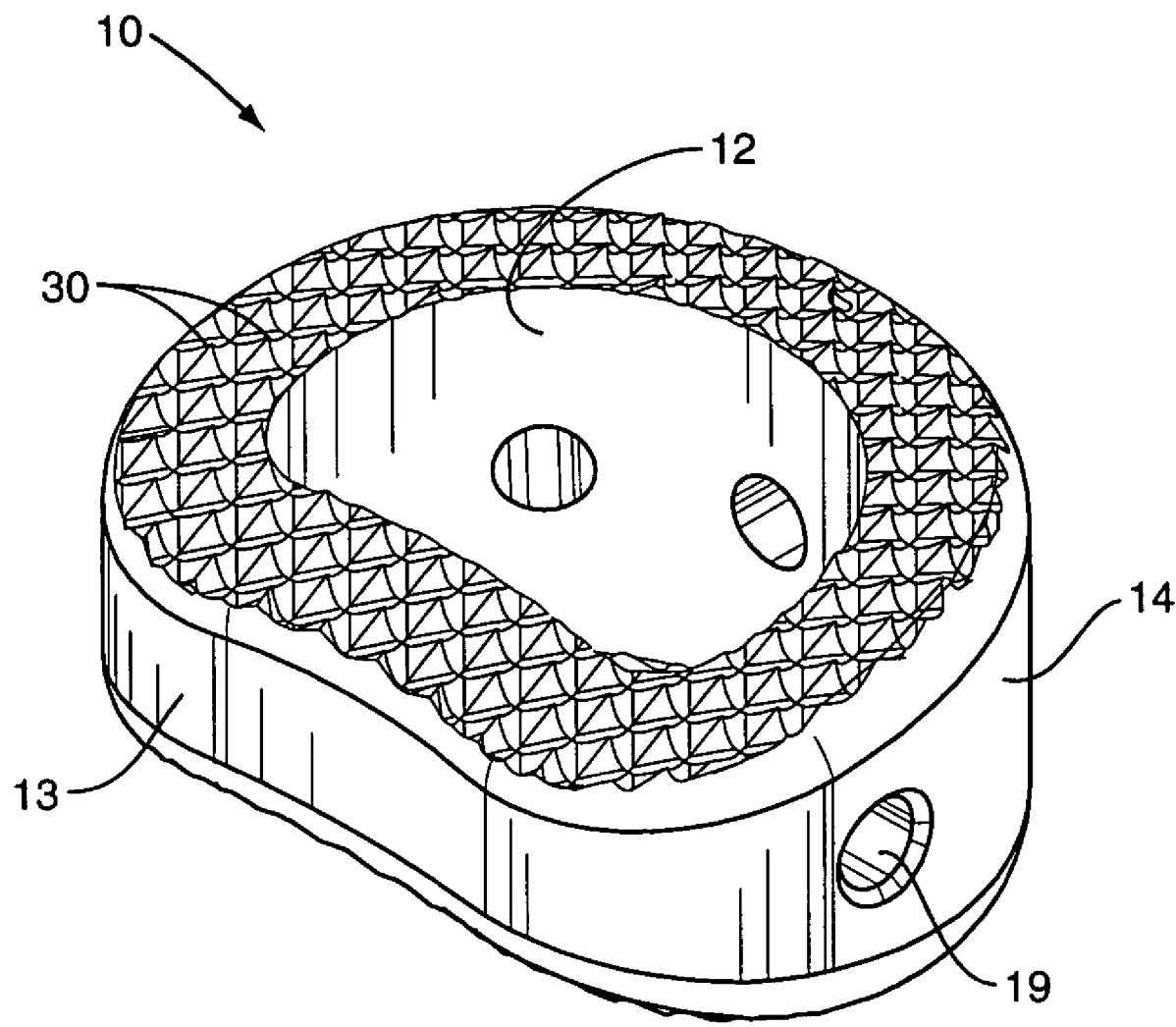
FIG. 1 is a perspective view of a spacer according to one embodiment of the present invention.

One embodiment of the present invention is directed to an interbody spacer 10 for insertion between vertebral members. The spacer 10 includes a body having inferior 18 and superior 17 faces. Teeth 30 are positioned along at least of one of the faces 17, 18 to maintain the position relative to the vertebral members. The teeth 30 are aligned in a pattern over all or part of at least one of the faces 17, 18.

FIG. 1 illustrates one embodiment of the spacer 10 having an annular shape forming an opening 12. The spacer 10 is formed by opposing posterior and anterior walls 13, 14 with opposing side walls 15 to complete the ring shape. The anterior wall 14 has a greater height than the posterior wall 13 causing the spacer 10 to have a wedge shape. One or more apertures 19 may be positioned in the walls. The apertures 19 provide a means for grasping or moving the spacer 10 with an instrument during the surgical process. The apertures 19 may be threaded to mate with the instrument. The apertures 19 extend through the walls and may further provide an avenue to access the opening 12, such as for inserting bone-growth material.

Figure 2:
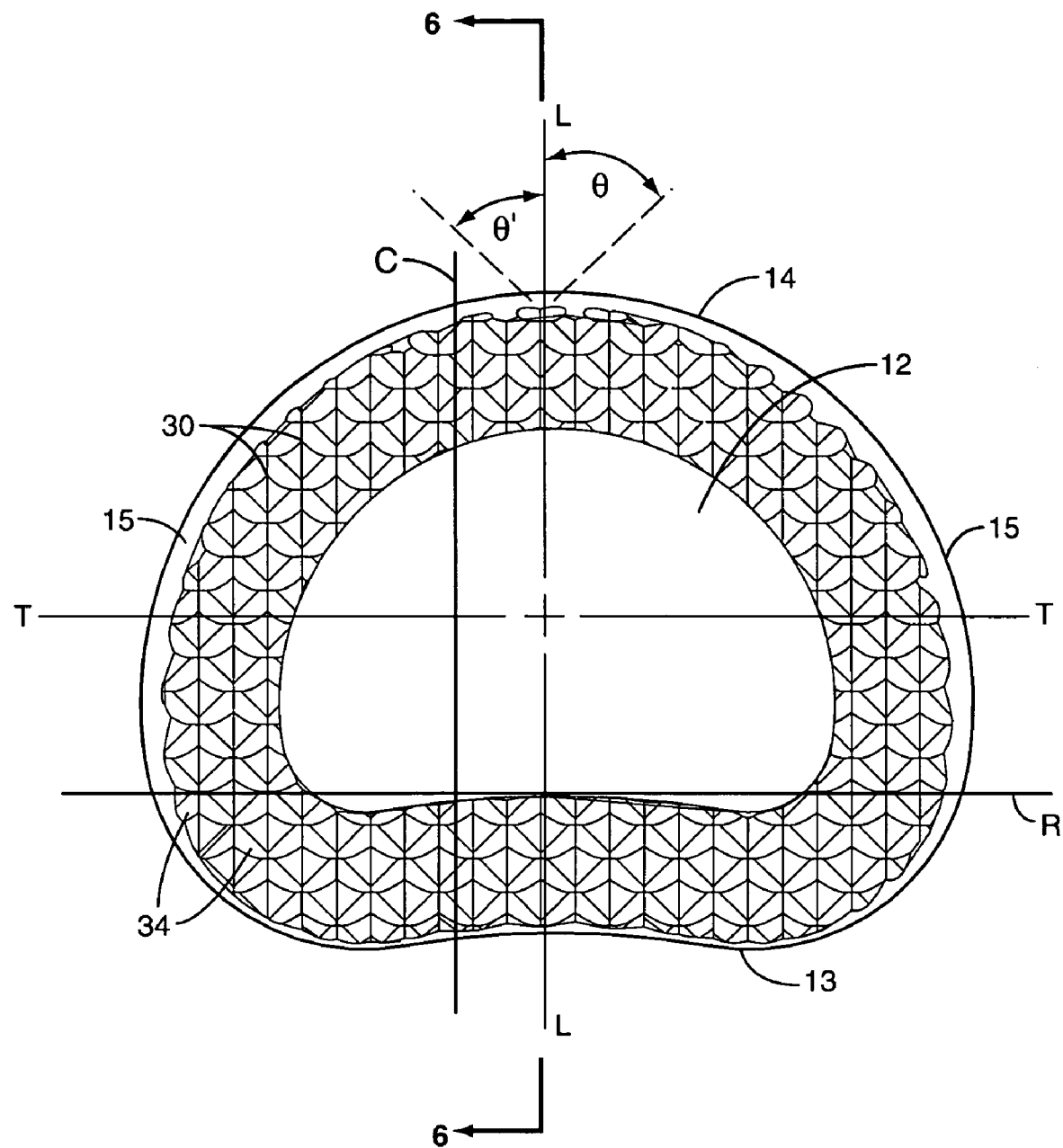
FIG. 2 is a top view of the spacer according to one embodiment of the present invention.

FIG. 2 illustrates a top view of the spacer 10 having a generally D-shape. This shape is created by the rounded anterior wall 14 and the substantially straight posterior wall 13. The interior wall of the opening 12 generally matches the shape of the outer walls and also has a generally D-shape. The thickness of the spacer walls formed between the outer walls of the opening 12 is generally uniform throughout the spacer 10. It is understood however that the spacer 10 and opening 12 may have a variety of different shapes, and the thickness of the spacer walls may independently vary, each being dependent upon the parameters of use.

A transverse plane is defined as being laterally aligned along the spacer and extending through the side walls 15. The transverse plane is substantially parallel to the transverse center line T-T. A longitudinal plane is defined as being aligned along the spacer 10 and extending through the anterior and posterior walls 14, 13. The longitudinal plane is substantially parallel to a longitudinal center line L-L.

Figure 3:
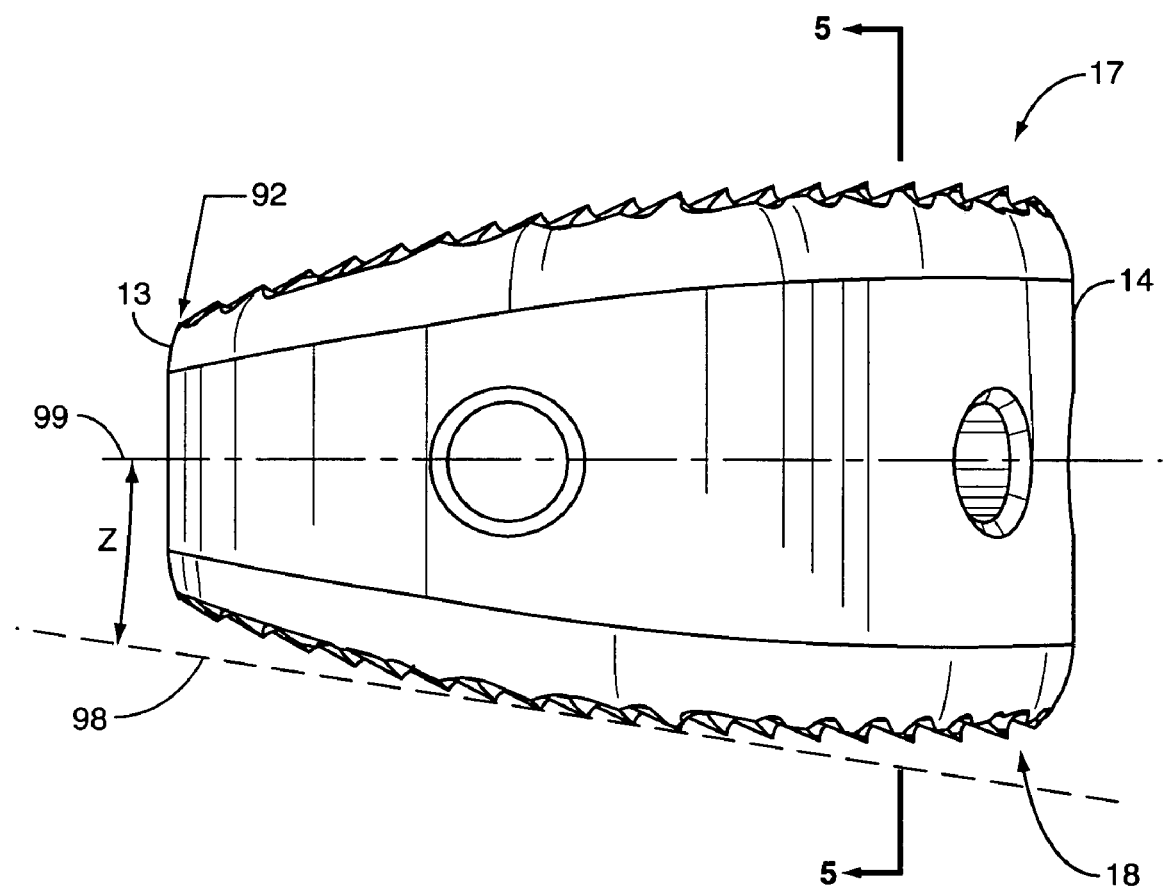
FIG. 3 is a side view of the spacer according to one embodiment of the present invention.

FIG. 3 illustrates a side view of the spacer 10 that more clearly illustrates the wedge shape formed by the taller anterior wall 14 and shorter posterior wall 13. The superior face 17 and inferior face 18 are generally convex when the spacer 10 is viewed from the side. The maximum height is located inward from the anterior wall 14 (i.e., at a point between the anterior wall 14 and posterior wall 13). In the embodiment illustrated in FIG. 3, the maximum height is located closer towards the anterior wall 14. The spacer 10 may be substantially uniform about a side centerline 99. Therefore, a distance between the centerline 99 and the inferior face 18 is the same as a corresponding distance between the centerline and the superior face 17. A line 98 tangent to the centerline 99 forms an angle Z. This angle may range from about 2° to about 7.5°. Because the spacer 10 is uniform about the centerline 99, a complimentary and equal second angle is formed between the superior face 17 and the centerline 99 (not shown). Therefore, an overall spacer angle formed between tangent lines for the inferior and superior faces 18, 17 may range from between about 4° to about 15°.

Figure 4:
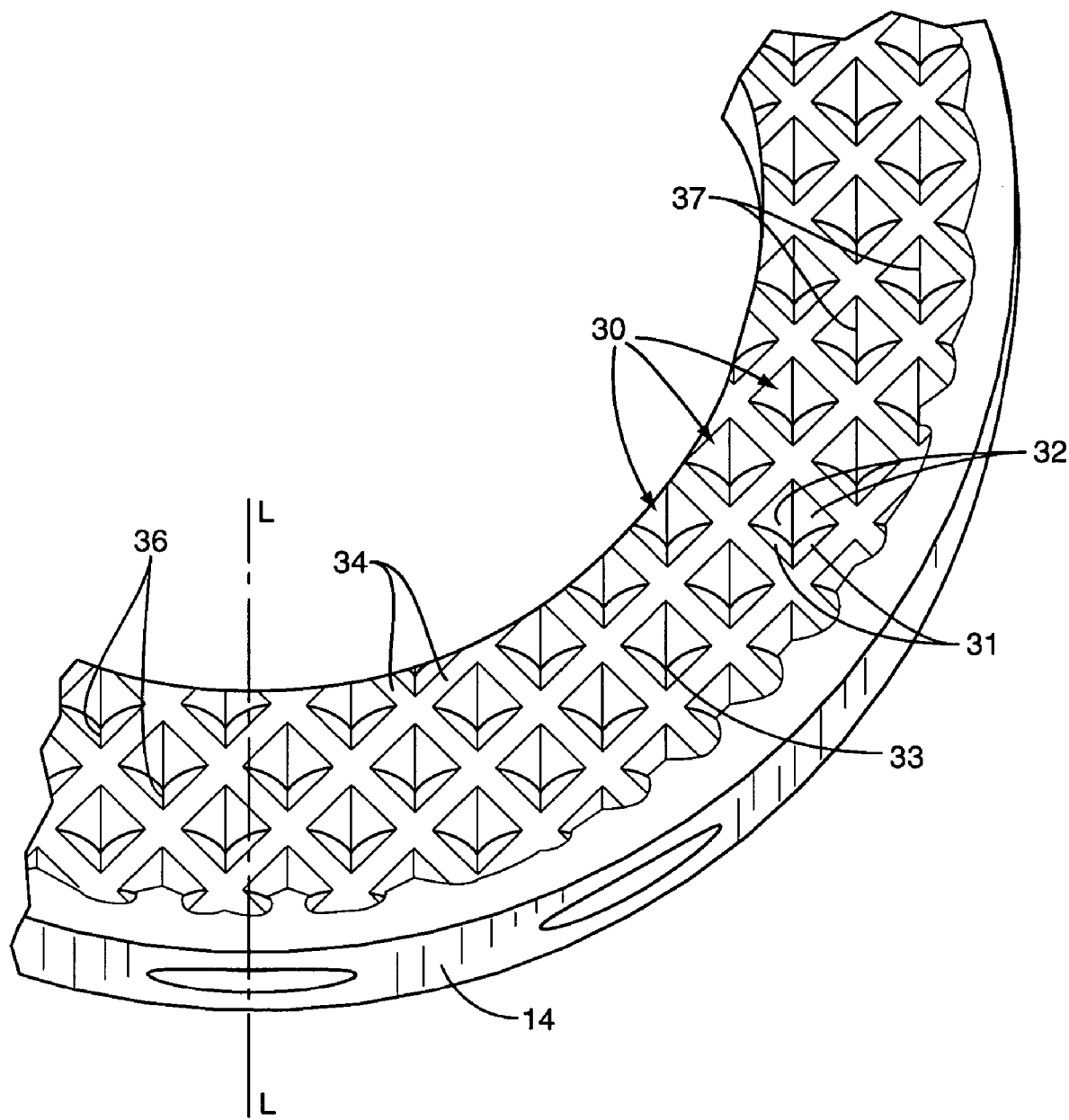
FIG. 4 is an enlarged partial perspective view of a plurality of teeth on the face of the spacer according to one embodiment of the present invention.

A plurality of teeth 30 are positioned on one or both of the inferior or superior faces 18, 17. FIG. 4 illustrates a view of one embodiment of teeth 30 each having two anterior surfaces 31 that face towards the anterior side 14 of the spacer 10. The anterior surfaces 31 are angled relative to each other and connect along a common anterior edge 36. Each tooth 30 further has two posterior surfaces 32 that face towards the posterior side 13 of the spacer 10. The posterior surfaces 32 are angled relative to each other and connect along a common posterior edge 37. In the embodiment of FIG. 4, each tooth 30 is substantially rectangular and is formed by four sides bounded on each side by a pathway 34. Each tooth 30 further includes a peak 33 at the intersection of the anterior and posterior surfaces 31, 32.

Figure 5:
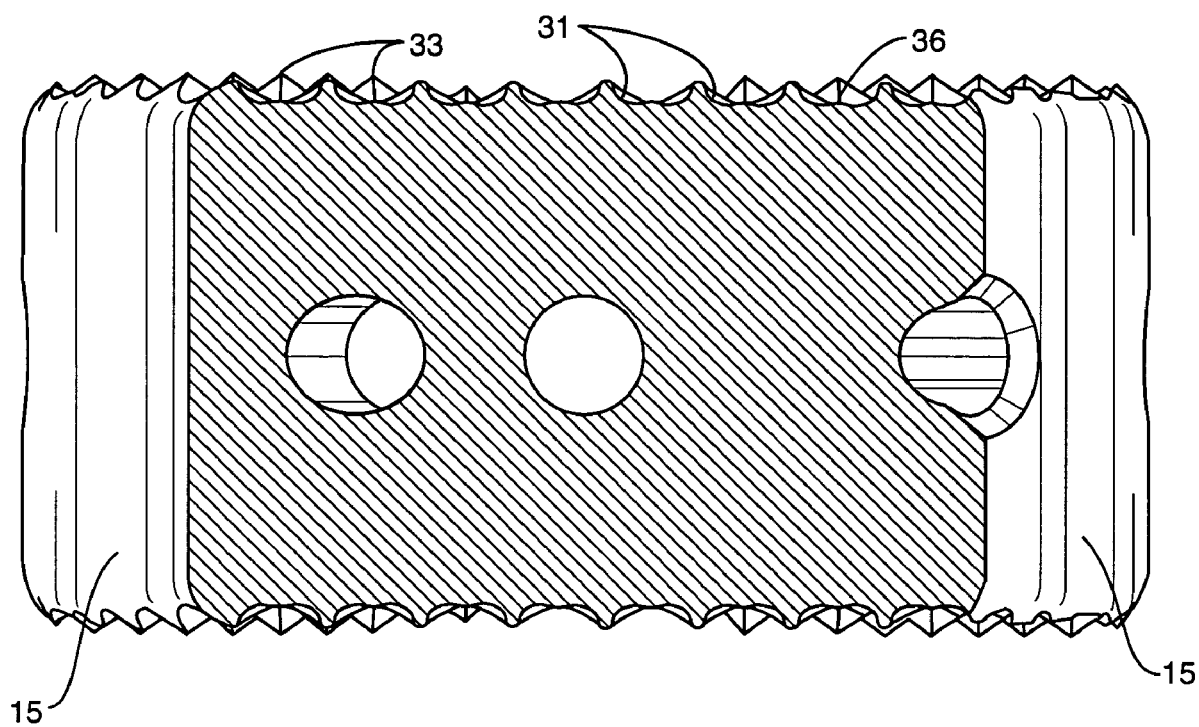
FIG. 5 is a cross-sectional view cut along line 5-5 according to one embodiment of the present invention.

FIG. 5 is a cross-sectional view cut along line 5-5 (see FIG. 3) in the transverse plane. The view cuts through a first row of teeth 30 and illustrates the peaks 33 of both the first row and an adjacent second row. The adjacent rows of teeth 30 are offset such that the peaks 33 of a first row are aligned within valleys of an adjacent second row. The bottom of the valleys are located in the pathways 34 extending between the teeth 30. The posterior surfaces 32 are curved forming a rounded posterior edge 37.

Figure 6:
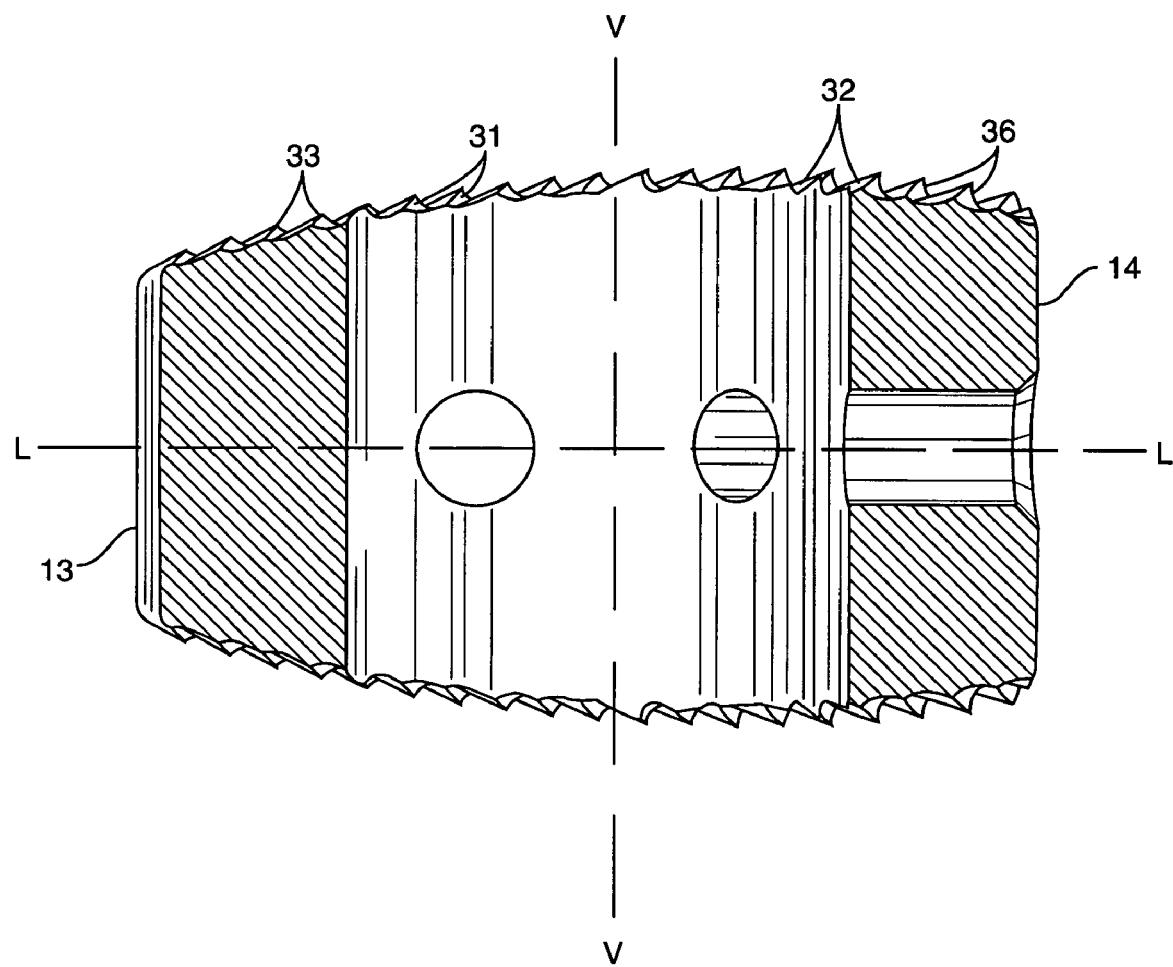
FIG. 6 is a cross-sectional view cut along line 6-6 according to one embodiment of the present invention.

FIG. 6 is a cross-sectional view cut along line 6-6 (see FIG. 2) in the longitudinal plane. The view cuts through a first column of teeth 30 and illustrates the peaks 33 of both the first column and the adjacent second column. The adjacent columns of teeth 30 are offset such that the peaks 33 of the first column are aligned within valleys of the adjacent second column. The bottoms of the valleys are aligned within the pathways 34 extending between the teeth 30.

The teeth 30 are ramped in an anterior direction caused by the posterior surfaces 32 having a lesser angle than the anterior surfaces 31 when viewed along the longitudinal plane. Further, the anterior surfaces 31 are curved and undercut the posterior surfaces 32 causing the peak 33 to face in an anterior direction. This configuration provides for inserting the spacer 10 using an anterior approach. The slighter angle of the posterior surfaces 32 and anterior angle of the peak 33 do not catch during the insertion process. Once the spacer 10 is inserted in the disc space between the vertebral members, the greater angle of the anterior surfaces 31 and the anterior facing peak 33 prevent or limit anterior movement of the spacer 10. The embodiments illustrated in FIGS. 1-6 include teeth 30 orientated for an anterior insertion approach. Other embodiments may include the teeth 30 oriented in different directions for a different insertion approach.

The pathways 34 extend in a crisscross pattern across the face of the spacer 10. The pathways include a series of first parallel pathways extending across the face in a first direction, and a series of second parallel pathways extending in a second direction. Each series of pathways 34 are substantially straight and form an angle relative to the longitudinal and transverse planes. In the embodiment of FIG. 2, first pathways are cut at angle Θ' relative to the longitudinal plane. Second pathways are cut at a mirrored angle Θ relative to the longitudinal plane. A mirrored angle is a negative equivalent to a first positive angle. By way of example, the first pathways are formed at an angle of about 45°, and the second pathways are formed at an angle of about −45°, each relative to the longitudinal plane.

The pathways 34 may be flat, angled into the face of the spacer 10, or a combination of both shapes. Specific embodiments include a U-shaped pathway, and a J-shaped pathway. In one embodiment, the first pathway has a first shape, and the second pathway has a second shape different than the first.

The plurality of teeth 30 and pathways 34 form a uniform pattern as best seen in FIG. 2. The teeth 30 are arranged in a series of columns generally aligned along the longitudinal plane. A straight line C can be drawn through the peaks 33 of each of the teeth 30 in a column. In one embodiment, the line C is substantially parallel with the longitudinal centerline L-L. The teeth 30 are also arranged in a series of rows generally aligned along the transverse plane. A straight line R can be drawn through the peaks 33 of each of the teeth 30 in a row. In one embodiment, the line R is substantially parallel with the transverse centerline T-T. Intersections of the first and second pathways occur along the edges of the teeth. In the embodiment of FIG. 2, the intersections are aligned with the lines C and R that extend across the spacer 10.

The teeth 30 are each aligned to face in the same direction with the posterior surfaces 32 and common posterior edge 37 having the same orientation. This is best illustrated in FIG. 2. The teeth 30 each work in combination as the spacer 10 is moved into the disc space. If various teeth 30 across the surface had different alignments, the teeth 30 would not work in unison during insertion. By way of example, if the teeth 30 on a first section of the face were aligned differently than teeth 30 on a second section, the spacer 10 would be more difficult to insert, and may move from the vertebral space.

Figure 7:
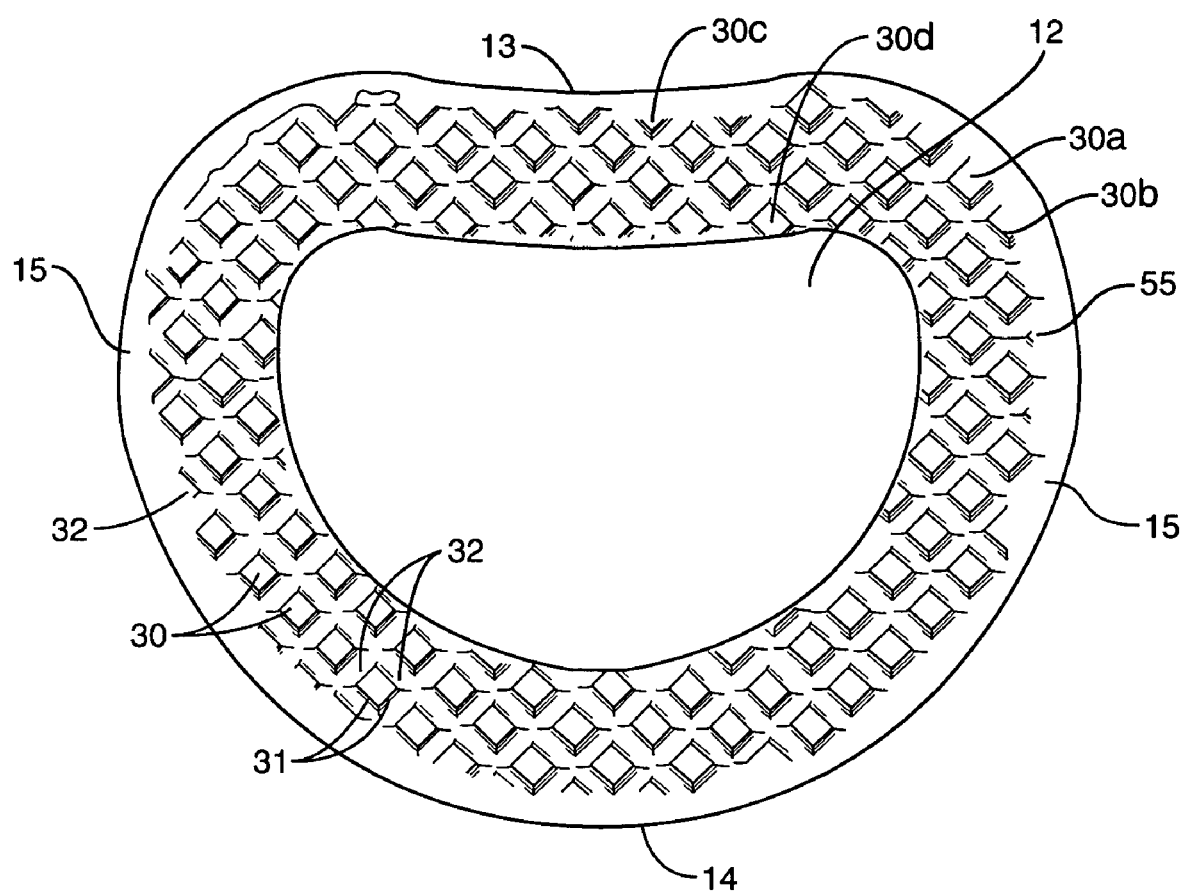
FIG. 7 is a top view of a spacer according to one embodiment of the present invention.
Figure 8:
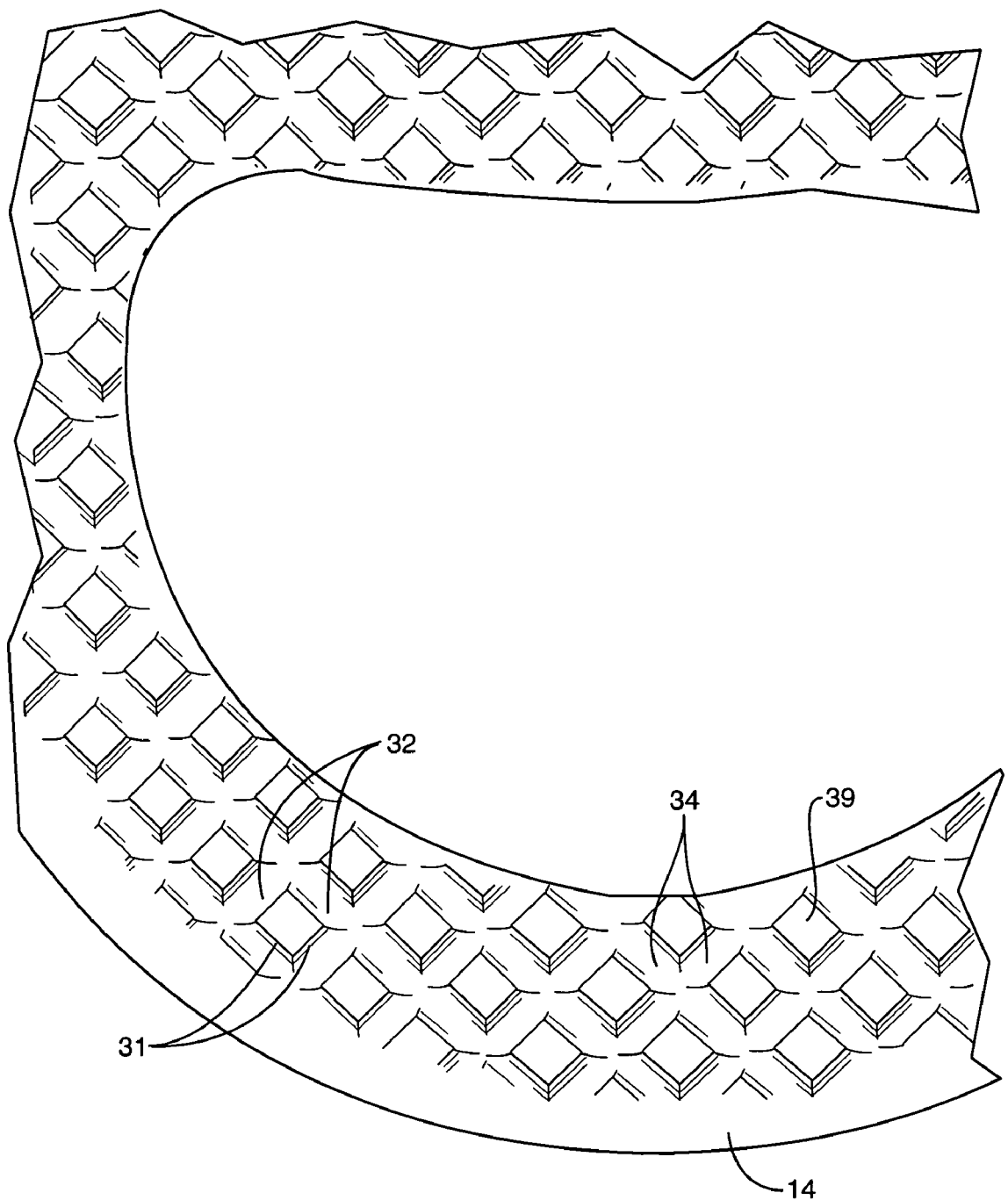
FIG. 8 is an enlarged partial perspective view of a plurality of teeth on the face of the spacer according to one embodiment of the present invention.

A second embodiment of teeth 30 is illustrated in FIGS. 7 and 8. The same reference numbers from the first embodiment are used to illustrate like elements. Each tooth 30 has a pair of anterior surfaces 31 aligned towards the anterior side 14 of the spacer 10, and a pair of posterior surfaces 32 aligned towards the posterior side 13. The teeth 30 each have a substantially rectangular shape. Each of the anterior and posterior surfaces 31, 32 extend outward and are capped by an outer surface 39. Pathways 34 extend in first and second directions and surround the teeth 30. In one embodiment, each of the outer surfaces 39 follows the convexity of the surface of the spacer 10. In this sense, the outer surface 39 is flat relative to the overall convex surface.

Each of the teeth 30 is aligned with the common posterior edges 37 each facing in the same direction. Further, each tooth 30 is aligned with the common anterior edges 36 each facing in the same direction. The teeth 30 may not be parallel to each other due to the overall convexity and angle of the superior and inferior faces 17, 18. In one embodiment, the spacer 10 is substantially uniform in each direction and can be used from a variety of insertion angles.

Figure 9:
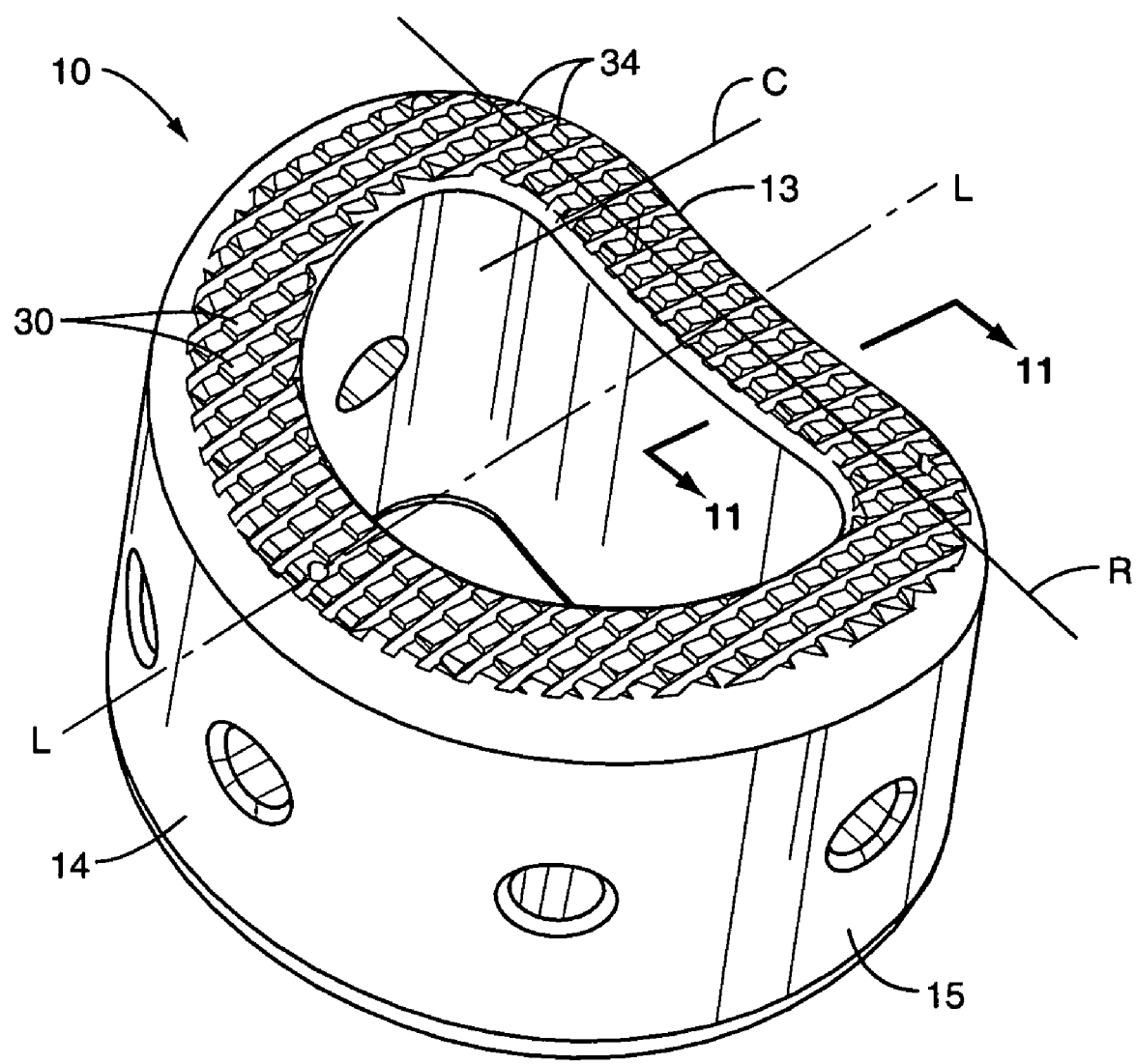
FIG. 9 is a perspective view of a spacer according to one embodiment of the present invention.
Figure 10:
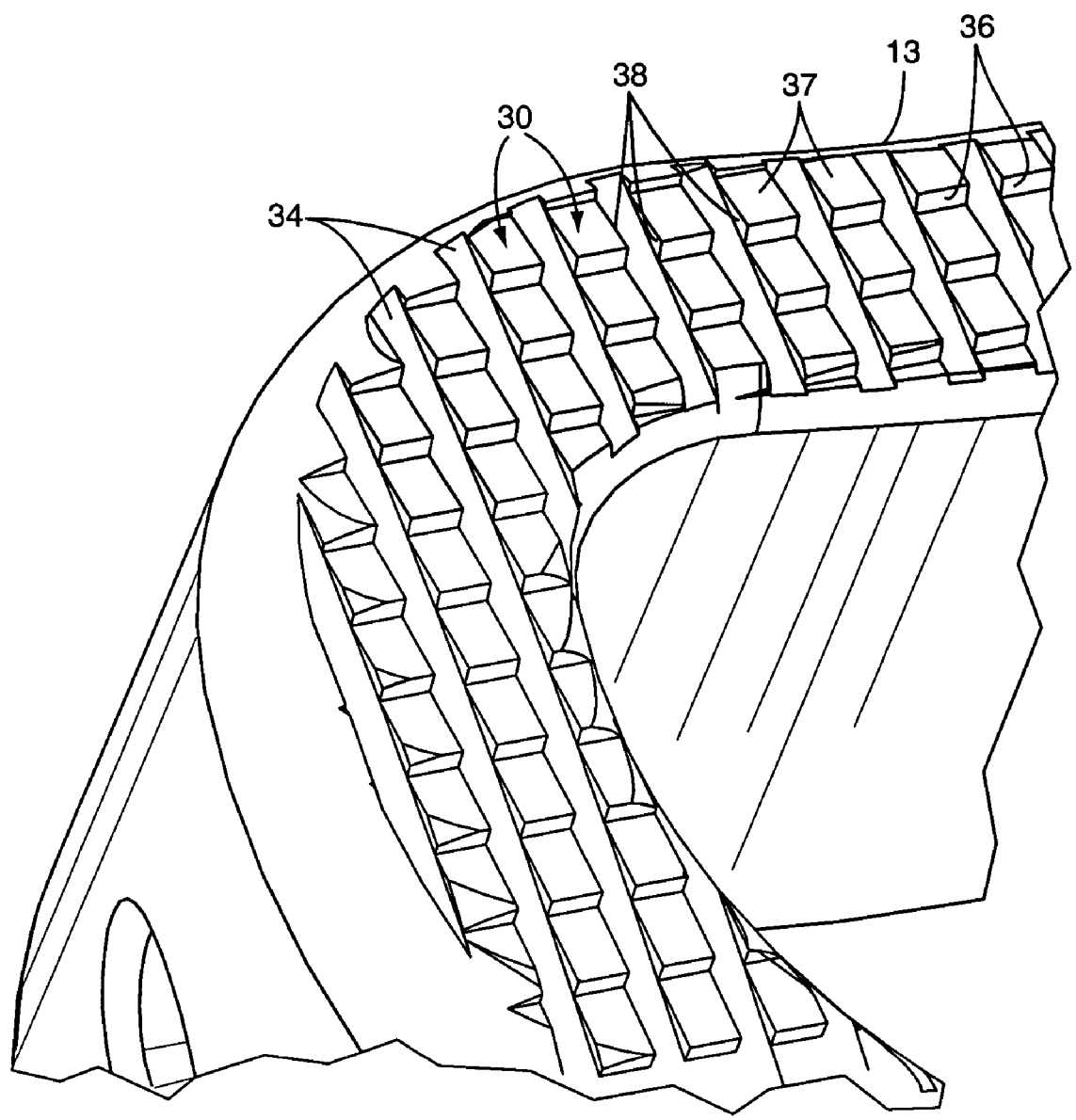
FIG. 10 is an enlarged partial perspective view of a plurality of teeth on the face of the spacer according to one embodiment of the present invention.
Figure 11:
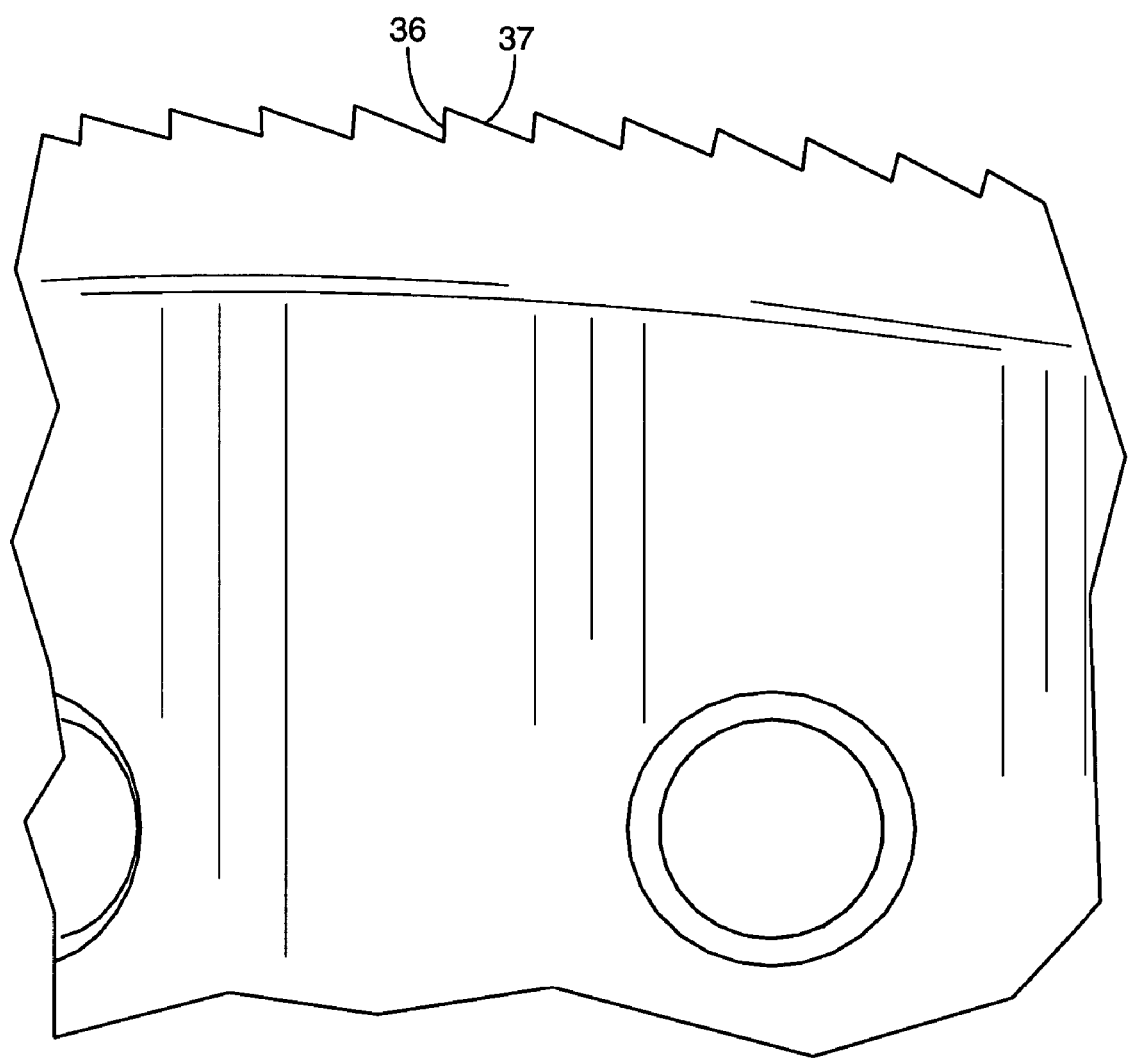
FIG. 11 is a partial cross-sectional view cut along line 11-11 according to one embodiment of the present invention.

FIGS. 9-11 illustrate a third tooth embodiment. Again, the same reference numbers from the first embodiment are used to illustrate like elements. Anterior and posterior sides 14, 13 are separated by side walls 15 to form an opening 12. Teeth 30 may be positioned on the face in a uniform pattern aligned in a plurality of columns such as along line C and rows such as along line R.

Each of the teeth 30 has four sides that form an overall rectangular shape. A posterior surface 37 is opposed by anterior surface 36 with side surfaces 38 extending along each side. The posterior 37 and anterior 36 surfaces are substantially the same width, as are the side surfaces 38. The posterior surface 37 extends outward from the spacer 10 at a lesser angle than the posterior surface 37. In one embodiment, the posterior surface 37 has an angle of about 70°, and the anterior surface 36 has an angle of about 0° (i.e., the anterior surface 36 is substantially perpendicular to the pathways). In one embodiment, the side surfaces 38 extend outward from the spacer at about 0°. In these embodiments, the angle of the surfaces is determined relative to the substantially flat pathways 34.

The teeth 30 are aligned in columns such as depicted by line C of FIG. 9. The teeth 30 are aligned with no gap being formed between the anterior surface 36 of a first tooth 30 and the posterior surface 37 of an adjacent second tooth. As illustrated in FIG. 11, this spacing forms a substantially saw-tooth orientation. Each of the columns on the face of the spacer 10 is aligned in the same direction. In one embodiment, the columns are each substantially parallel with the longitudinal center line L-L. Teeth 30 are also aligned in row as depicted by line R in FIG. 9. In one embodiment, the rows are substantially perpendicular to the columns, and may be perpendicular to the longitudinal center line L-L.

Pathways 34 are positioned between each of the columns of teeth 30. In one embodiment, pathways 34 have a width less than the width of the teeth 30 (i.e., less than the width of the anterior 36 and posterior 37 surfaces).

The teeth 30 of the third embodiment are sized and configured to an anterior insertion approach. The angle of the posterior surfaces 37 is set to facilitate movement of the spacer 10 into the disc space from the anterior side. The anterior surface 36 has a steeper angle to prevent the spacer 10 from moving out of the disc space after insertion. As with the other embodiments, the teeth 30 may be aligned in other orientations for other insertion approaches.

The outer edges of the spacer 10 may have a round or curved configuration that prevent a sharp angle that may make the insertion of the spacer 10 more difficult, or cause injury to the patient. In one embodiment as illustrated in FIG. 3, the spacer 10 has a radius 92 extending along the exterior edges where the inferior and superior faces 18, 17 meet the side walls 15 and posterior and anterior walls 13, 14. Specific embodiments include radiuses of between about 2 mm and 3 mm. The teeth 30 adjacent to the edges may fall within the radius area and be rounded or curved. By way of example as illustrated in FIG. 7, tooth 30a which slightly overlaps into the edge of the face has a rounded section within the edge of the spacer 10. Tooth 30b is positioned closer to the edge and therefore has a larger rounded section. Tooth 30c is almost completely positioned within the edge and therefore is almost completely rounded. Teeth 30 positioned along the opening 12 may also include rounded sections, as illustrated by tooth 30d.

The spacer 10 may be constructed of a single piece with the teeth 30 formed into one or both faces 17, 18. Alternatively, the teeth 30 may be constructed of a separate material and attached to the faces 17, 18.

One embodiment of the spacer (e.g., FIG. 3) illustrates each of the inferior and superior surfaces having a convex shape. Other embodiments may also include substantially flat surfaces, or concave surfaces. Further, the spacer may have surfaces of different shapes with the inferior surface having a first shape and the superior surface having a second shape (e.g., convex inferior surface and substantially flat superior surface).

The term vertebral member is used generally to describe the vertebral geometry comprising the vertebral body, pedicles, lamina, and processes. The spacer 10 may be sized and shaped, and have adequate strength requirements to be used within the different regions of the vertebra including the cervical, thoracic, and lumbar regions.

Bone growth material may be positioned within the opening 12 to facilitate bone growth through the spacer 10. The bone growth material may include a sponge, matrix, and/or other carrier impregnated with a protein such as bone morphogenic protein (BMP), LIM mineralization protein (LMP), etc.

The present invention may be carried out in other specific ways than those herein set forth without departing from the scope and essential characteristics of the invention. The teeth 30 may further be spaced inward from the edges of the faces 17, 18. A gap 55 may exist along the edge of the faces that does not include any teeth 30. The spacer 10 may have a variety of shapes and sizes. In one embodiment, the spacer includes an interior wall that closes the opening. In another embodiment, the spacer does not include an opening 12. In embodiments with teeth 30 on both the inferior and superior faces 18, 17, the teeth 30 may be aligned in a common direction on each of the faces. The present embodiments are, therefore, to be considered in all respects as illustrative and not restrictive, and all changes coming within the meaning and equivalency range of the appended claims are intended to be embraced therein.

What is claimed is:

1. An interbody spacer comprising:
a member having first and second faces;
a plurality of first pathways on the first face each extending at an acute angle relative to a longitudinal center line of the spacer and a plurality of second pathways on the first face each extending at a mirrored acute angle relative to the longitudinal center line, the longitudinal center line extending through anterior and posterior sides of the spacer, each of the plurality of first and second pathways being straight; and
teeth extending outward from the first face between the plurality of first and second pathways;
each of the teeth including first and second straight sides at the first face with each of the first straight sides being parallel with the plurality of first pathways and each of the second straight sides being parallel with the plurality of second pathways.

2. The spacer of claim 1, wherein the plurality of first and second pathways and the teeth form a uniform repeating pattern on the first face.

3. The spacer of claim 1, wherein the first plurality of pathways extend on the first face at an angle of about 45° relative to the longitudinal center line, and the second plurality of pathways extend on the first face at an angle of about −45° relative to the longitudinal center line.

4. The spacer of claim 1, wherein the teeth further comprise a peak angled in an anterior direction.

5. The spacer of claim 1, wherein the member has an annular shape with a central opening.

6. The spacer of claim 1, wherein the teeth comprise a pair of angled anterior surfaces and a pair of angled posterior surfaces.

7. The spacer of claim 1, wherein the first and second faces are convex.

8. The spacer of claim 7, wherein a high point of the first and second faces is positioned between the anterior side and an inner edge of a central opening.

9. The spacer of claim 1, wherein the edges are radiused having a rounded configuration.

10. The spacer of claim 9, wherein at least one of the plurality of teeth adjacent to the edges have a rounded configuration.

11. The spacer of claim 1, wherein the first and second faces have substantially the same angle relative to a centerline.

12. An interbody spacer comprising a plurality of teeth on a first face, each of said plurality of teeth having first and second anterior faces that meet at a top point, the plurality of teeth being aligned in columns with a first line extending through each of the top points in a first column being substantially parallel with a second line extending through each of the top points in a second column, the first and second columns being adjacent to each other on the first face, each of the first and second lines being substantially parallel to a longitudinal centerline extending through anterior and posterior sides of the spacer, each of the teeth in the first and second columns being separated by valleys, the plurality of teeth in the first and second columns being offset such that a row of top points aligned along a third line substantially perpendicular to the longitudinal centerline includes the top point of a tooth from only one of the first and second columns.

13. The spacer of claim 12, wherein the top point is a peak having a substantially V-shape when viewed in a transverse direction.

14. The spacer of claim 12, wherein the first and second anterior faces of each of the plurality of teeth intersect at a common anterior edge, with the common anterior edge of the teeth in the first column falling within the first line.

15. The spacer of claim 12, wherein the first anterior edge is angled at about 45° relative to a longitudinal center line extending through anterior and posterior walls of the spacer, and the second anterior edge is angled at about −45° relative to the longitudinal center line.

16. The spacer of claim 12, wherein each of the plurality of teeth further comprise first and second posterior surfaces.

17. The spacer of claim 12, wherein the plurality of teeth are aligned in rows with a fourth line extending through each of the top points in a first row being substantially parallel with a fifth line extending through each of the top points in a second row.

18. The spacer of claim 17, wherein each of the fourth and fifth lines are substantially perpendicular to the longitudinal centerline.

19. The spacer of claim 12, wherein the first face is convex.

20. The spacer of claim 19, wherein a high point on the first face is positioned inward of an anterior edge of the spacer.

21. The spacer of claim 12, wherein the spacer has an annular shape with a central opening.

22. The spacer of claim 21, wherein the spacer is substantially D-shaped with a curved first wall and a substantially straight second wall.

23. An interbody spacer comprising:
a body having an anterior side and a posterior side, and first and second faces;
teeth on the first face of the body, each of the teeth being substantially rectangular in shape and having two anterior surfaces facing towards the anterior side and two posterior surfaces facing towards the posterior side;
the teeth aligned in a pattern of rows and columns, a center point of each of the teeth aligned in a first row being centered with a gap formed between each of said plurality of teeth in an adjacent second row, and the center point of each of said plurality of teeth in a first column being centered within the gap formed between each of said plurality of teeth in an adjacent second column, the first row including the center point of a tooth from only one of the first and second columns, the first column including the center point of a tooth from only one of the first and second rows, the rows and columns being substantially perpendicular to each other;
the columns each being parallel with a longitudinal centerline of the body and each of the rows being perpendicular to the longitudinal centerline of the body.

24. The spacer of claim 23, wherein the body has an annular shape with a central opening.

25. The spacer of claim 24, wherein a maximum height of the body is positioned between the anterior side and a transverse centerline.

26. The spacer of claim 23, wherein the first and second faces are convex.

27. The spacer of claim 23, further comprising the teeth positioned on the second face.

* * * * *